United States Patent [19]

Iida

[11] Patent Number: 4,663,973

[45] Date of Patent: May 12, 1987

[54] ULTRASONIC SCANNING APPARATUS

[75] Inventor: Taketoshi Iida, Tochigi, Japan

[73] Assignee: Kabushiki Kaisha Toshiba, Kawasaki, Japan

[21] Appl. No.: 817,271

[22] Filed: Jan. 8, 1986

[30] Foreign Application Priority Data

Jan. 10, 1985 [JP] Japan .................................. 60-2462

[51] Int. Cl.$^4$ .......................................... G01N 29/00
[52] U.S. Cl. ...................................... 73/626; 73/609; 73/628
[58] Field of Search ................. 73/625, 626, 609, 628; 128/660

[56] References Cited

U.S. PATENT DOCUMENTS

| | | | |
|---|---|---|---|
| 3,919,683 | 11/1975 | Itamura et al. | 340/1 R |
| 4,235,111 | 11/1980 | Hassler | 73/626 |
| 4,257,271 | 3/1981 | Glenn | 73/626 |
| 4,392,379 | 7/1983 | Yamaguchi | 73/626 |
| 4,505,156 | 3/1985 | Questo | 73/626 |
| 4,534,359 | 8/1985 | Miller-Jones et al. | 73/626 |

FOREIGN PATENT DOCUMENTS

7724213  8/1977  France.
1503532  3/1978  United Kingdom.

OTHER PUBLICATIONS

Gabel et al., "Hybrid Time-Delay/Phase-Shift Digital Beamforming for Uniform Collinear Arrays," J. Acoust. Soc. Am. 75(6), pp. 1837-1947, Jun. 1984.

Primary Examiner—Howard A. Birmiel
Attorney, Agent, or Firm—Finnegan, Henderson, Farabow, Garrett & Dunner

[57] ABSTRACT

An ultrasonic scanning apparatus includes a transducer array made up of a plurality of ultrasonic transducer elements and delay lines connected through individual switch elements to the transducer elements. The transducer array, the switch elements and the delay lines are each divided into two blocks. The ultrasonic echo signals derived from these blocks are summed through the corresponding delay lines. One of the summed signals of both the blocks is applied through a fixed delay line to an adder. The other of the signals is directly applied to the adder. The adder adds together these echo signals.

8 Claims, 7 Drawing Figures

(DEFLECTION ANGLE OF RECEIVING BEAM)

(DEFLECTION ANGLE 0 TO +θ)

(DEFLECTION ANGLE OF RECEIVING BEAM)

(DEFLECTION ANGLE 0 TO $-\theta$)

ULTRASONIC SCANNING APPARATUS

BACKGROUND OF THE INVENTION

The present invention relates to an ultrasonic scanning apparatus of the sector scan type.

The ultrasonic scanning apparatus is generally categorized into a sector scan type scanning apparatus and a linear scan type scanning apparatus. In the ultrasonic scanning apparatus of the sector scan type, an ultrasonic probe containing an ultrasonic transducer array sectionally scans an object, using the ultrasonic beam projected from the probe. The image information contained in the echo-wave from the object is displayed on the CRT screen. Since only the echo-waves corresponding to the focal points are received, the echo signals from the transducer elements are delayed by different periods of time. To obtain such delay periods in the conventional probe, N transducer elements arrayed channel 1 to channel N are connected by N switching elements to a delay line. The N switching elements have each n switching contacts. The contacts of the switching elements are coupled with n terminals of the delay line. These contacts are switched according to a deflection angles 0° to $\pm\theta°$ of the ultrasonic beam, so that the echo-wave as specified by each deflection angle can be received.

The conventional switching circuit requires the same number of contacts for each switching element as that of the terminals of the delay line. The number of the terminals of the switching element depends on a maximum deflection angle. Accordingly, for a large deflection angle, a great number of the terminals are needed. The more terminals the more contacts for the switching elements. The switching element with such an increased number of contacts is inevitably large. The large switching element has a large stray capacitance. Electrically, this brings about the crosstalk problem, and degradation of the frequency characteristic of the ultrasonic imaging apparatus.

SUMMARY OF THE INVENTION

Accordingly, an object of the present invention is to provide an ultrasonic scanning apparatus which requires a reduced number of terminals of the delay line and a reduced number of the switching contacts of the switching elements, which are connected to the terminals of the delay line.

According to the present invention, there is provided an ultrasonic scanning apparatus having a transducer array made of a plurality of ultrasonic transducer elements and delay line means connected by individual switching elements to the transducer elements. The transducer array, the switching elements, and the delay line are each divided into two blocks. The ultrasonic echo signals derived from these blocks are summed through the corresponding delay line section. One of the summed signals of both the blocks is applied through a fixed delay line to an adder. The other of the signals is directly applied to the adder. The adder adds together these echo signals.

DETAILED DESCRIPTION OF THE PREFERRED EMBODIMENT

Figure 1:
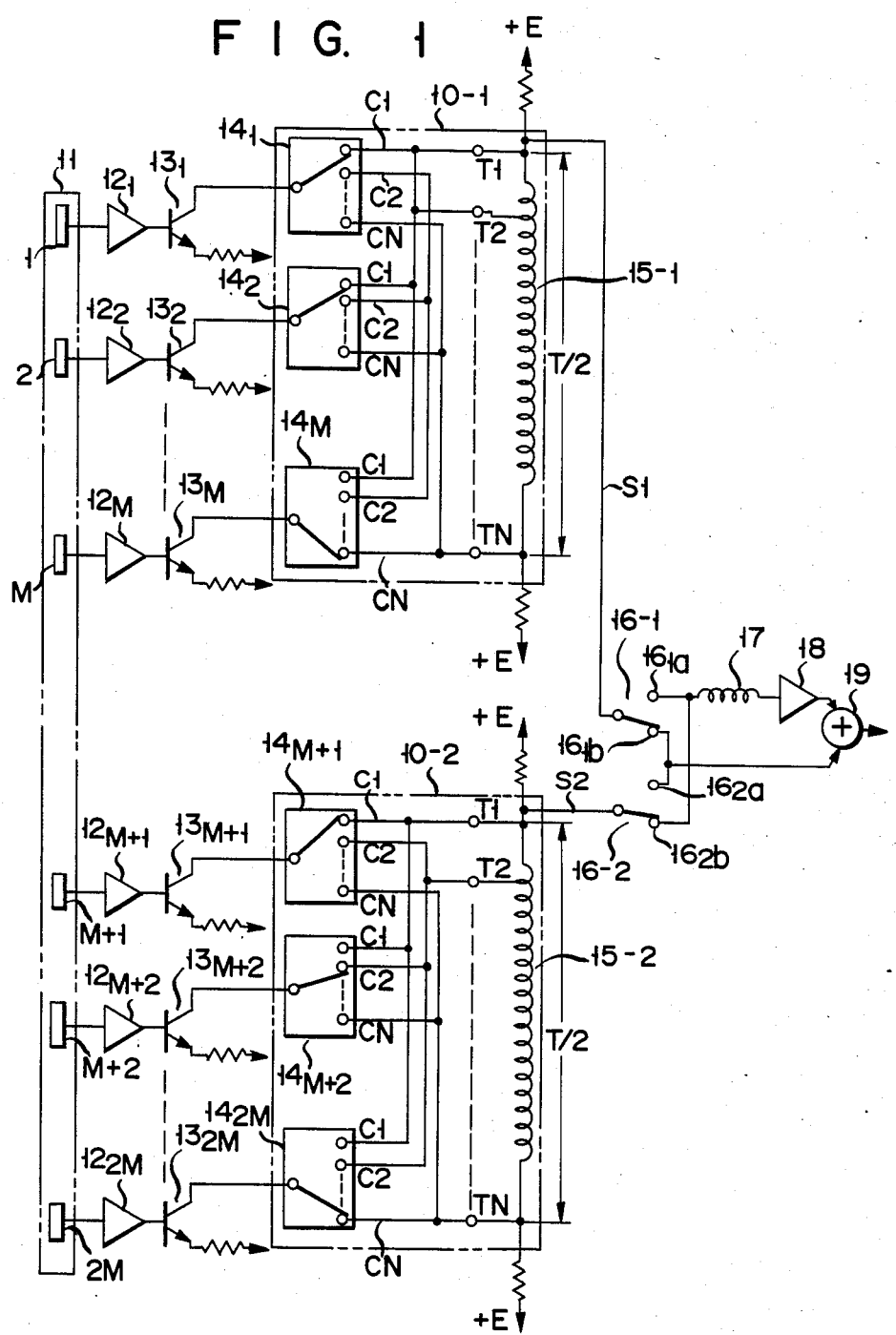
FIG. 1 is a circuit diagram of an ultrasonic scanning apparatus according to an embodiment of the present invention.

According to an ultrasonic scanning apparatus shown in FIG. 1, an ultrasonic probe 11 includes a plurality of ultrasonic transducer elements 1 to 2M. This probe is divided into two blocks, a first block and a second block. The first block includes ultrasonic elements 1 to M. The second block includes ultrasonic elements M+1 to 2M. The ultrasonic transducer elements 1 to M in the first block are respectively connected through amplifiers $12_1$ to $12_M$ to the bases of switching transistors $13_1$ to $13_M$. The ultrasonic transducer elements M+1 to 2M in the second block are respectively connected through amplifiers $12_{M+1}$ to $12_{2M}$ to the bases of switching transistors $13_{M+1}$ to $13_{2M}$.

The collectors of switching transistors $13_1$ to $13_M$ connected to the common contacts of selectors, i.e., switching elements $14_1$ to $14_M$ in first circuit block 10-1, respectively. The collectors of switching transistors $13_{M+1}$ to $13_{2M}$ are connected to the common contacts of switching elements (e.g. analog switches TC4051 manufactured by TOSHIBA CORP. Japan) $14_{M+1}$ to $14_{2M}$ in the second circuit block 10-2, respectively. The output contacts C1 to CN of switching elements $14_1$ to $14_M$ are connected to terminals T1 to TN of delay line 15-1 with a delay time of a maximum of T/2. The output contacts C1 to CN of switching elements $14_{M+1}$ to $14_{2M}$ are connected to terminals T1 to TN of delay line 15-2 with a delay time of a maximum of T/2.

Each switching element selects one of output contacts C1 to CN in accordance with the deflection or steered angle and focal distance of the ultrasonic beam. It is determined, by using built-in programs, which element selects which output contact is programmed in accordance with the steered angle and focal distance.

The output terminals of the delay lines 15-1 and 15-2 are connected to the common terminals of switches 16-1 and 16-2. The contacts $16_{1a}$ and $16_{2b}$ of switches 16-1 and 16-2 are connected to adder 19, through fixed delay line 17 and amplifier 18. The contacts $16_{1b}$ and $16_{2a}$ of switches 16-1 and 16-2 are directly connected to adder 19.

Figure 2:
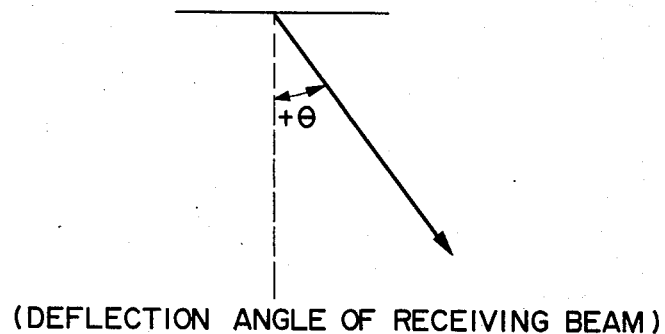
FIG. 2 shows a diagram for illustrating a characteristic of a delay time corresponding to deflection angles 0° to $\pm\theta°$ for the sector scan.

The operation of the ultrasonic scanning apparatus thus arranged will be described. When the ultrasonic beam sector scans from angles 0° to $+\theta°$, i.e. the half cycle, as shown in FIG. 2, switches 16-1 and 16-2 make contacts 16-1b and 16-2b. At this time, the echo signals from ultrasonic transducer elements 1 to M of the 1 to M channels are supplied to delay line 15-1 by way of switching elements $14_1$ to $14_M$ in the first block 10-1. Each of switching elements $14_1$ to $14_M$ is connected to one of contacts C1 to CN. The echo signals from transducer elements $14_1$ to $14_M$ are sequentially delayed minimum delay time 0 to maximum delay time T/2. Then, these signals are added, providing a signal S1. Signal S1 is input to adder 19 by way of contact $16_{1a}$.

In the ultrasonic scanning apparatus of this embodiment, the echo signals are formed by the currents selectively flowing through the collector-emitter paths of transistors $13_1$ to $13_M$ through switching elements $14_1$ to $14_M$. These currents flow when the output voltage signals of the ultrasonic transducer elements 1 to M are selectively fed to the bases of transistors $13_1$ to $13_M$.

The echo signals from ultrasonic transducer elements M+1 to 2M of M to 2M channels are supplied to delay line 15-2 by way of switching elements $14_{M+1}$ to $14_{2M}$ in the second circuit block 10-2. At this time, switching elements $14_{M+1}$ to $14_{2M}$ are respectively connected to contacts C1 to CN. The echo signals from transducer elements M+1 to 2M are sequentially delayed minimum delay time 0 to maximum delay time T/2. Then, these are added, providing a echo signal S2. Signal S2 is input to adder 19 by way of contact $16_{1a}$, fixed delay line 17 of T/2 delay, and amplifier 18.

Figure 3:
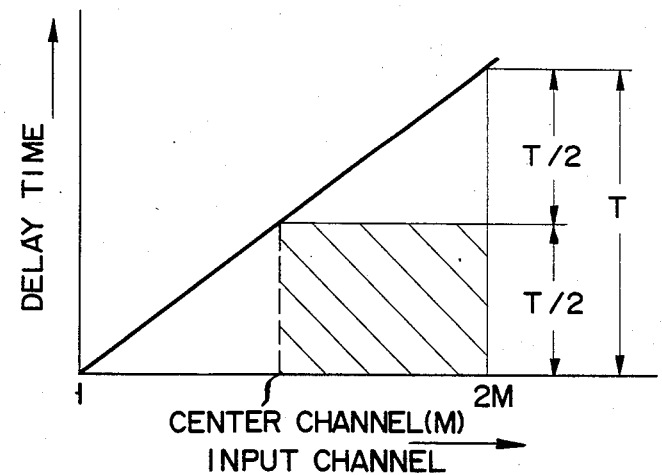
FIG. 3 shows a graph for illustrating a scanning angle of a receiving beam for the sector scan of angles 0° to $\pm\theta°$.
Figure 4:
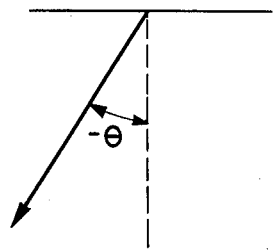
FIG. 4 shows a diagram for illustrating a characteristic of a delay time corresponding to deflection angles 0° to $-\theta°$ for the sector scan.

The signals S1 and S2 are maximumly delayed T/2 at the point of switches 16-1 and 16-2. Since the signal S2 passes through the fixed delay line 17 of T/2 delay, it is delayed a maximum of T. FIG. 3 shows a relationship between the delay time of the echo signal and channels 1 to M. In the figure, the solid line represents that relationship observed when the ultrasonic beam is deflected up to an angle $\theta°$. This rectilinear line is horizontally shifted with respect to the channel center (M) when switching elements $14_1$ to $14_{2M}$ are each sequentially switched from contacts C1 to CN. When the rectilinear line lies horizontally, all of the echo signals are delayed with the equal delay time (T/2). Under this condition, the ultrasonic beam is at the position of angle 0°.

When the ultrasonic beam is deflected or steered by angles 0° to $-\theta°$, switches 16-1 and 16-2 are connected to contacts $16_{1a}$ and $16_{2a}$. As in the case of the half cycle as mentioned above, the echo signals from transducer elements 1 to M of channels 1 to M are supplied to delay line 15-1, through switching elements $14_1$ to $14_M$ in the first circuit block 10-1. At this time, all of switching elements 1 to M have been connected to contacts C1. Therefore, the echo signals from transducer elements 1 to M are all added together in a delayed state. The added echo signal S1 is applied to adder 19, through fixed time delay time 17 and amplifier 18. Therefore, signal S1 delayed by time T/2 is applied to adder 19. Echo signals from transducer elements M+1 to 2M of channels M to 2M are supplied to delay line 15-2, via switching elements $14_{M+1}$ to $14_{2M}$ in the second circuit block 10-2. At this time, all of switching elements $14_{M+1}$ to $14_{2M}$ have been connected to contacts CN. Therefore, the echo signals from transducer elements M+1 to 2M are all delayed a maximum of T/2, and added together. The added echo signal S2 is directly applied to adder 19, from contact $16_{2a}$.

Figure 5:
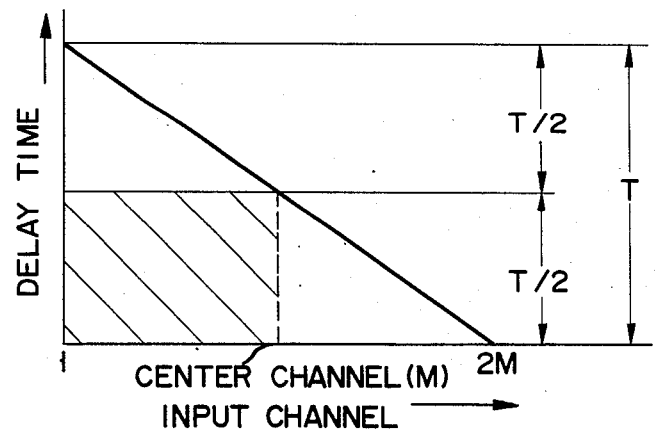
FIG. 5 shows a graph for illustrating a scanning angle of a receiving beam for the sector scan of angles 0° to $-\theta°$.

Under this condition, the signals S1 and S2 to adder 19 are delayed a maximum of T/2. This state indicates that the deflection angle of the ultrasonic beam is 0°. From this state, switching elements 14-1 to $14_M$ and $14_{M+1}$ to $14_{2M}$ are sequentially switched. The delay characteristic varies rectilinearly and downwardly to the right, as shown in FIG. 5, unlike the characteristic shown in FIG. 3. Specifically, switching elements 1 to M are each sequentially switched from contacts C1 to CN. The echo signals from transducer elements 1 to M are sequentially delayed 0 to T/2, and added together. The added echo signal S1 is input to adder 19, via contact $16_{1a}$, delay line 17 and amplifier 18. Echo signals $14_{M+1}$ to $14_{2M}$ of channels M to 2M are applied through the second circuit block 10-2 to delay line 15-2. At this time, switching elements $14_{M+1}$ to $14_{2M}$ are sequentially connected to contacts C1 to CN. With this switching operation, the echo signals from transducer elements M+1 to 2M are sequentially delayed times 0 to T/2, and added together. The added echo signal S2 is directly applied to adder 19, from contact $16_{2a}$.

Repeating the sequence of operations as mentioned above, the beam is deflected by angles $-\theta°$, 0° and $+\theta°$. In the above-mentioned embodiment, the echo signals from probe 11 with channels 1 to 2M are divided into two blocks, and these signals are processed. The delay time of the delay line is not required for covering all of the channels 1 to 2M, but is needed to cover only the half of the channels. Because of this feature, reduction of size of the delay line and cost to manufacture is realized. Further, the required number of terminals of switching elements is halved when compared with that of the conventional apparatus. The reduced number of the terminals naturally reduces the stray capacitance associated with the switching elements and the on resistance of the elements. As a consequence, influence by noise on the echo signals is decreased.

Another embodiment of the present invention will be described referring to FIG. 6. In the figure, the output terminals of delay lines 15-1 and 15-2 in the first and second circuit blocks 10-1 and 10-2 are connected to common terminals of switches 16-1 and 16-2. The contacts $16_{1b}$ and $16_{2a}$ of switches 16-1 and 16-2 are interconnected and then to the output terminal. Contact $16_{1a}$ of switch 16-1 is connected to a maximum delay terminal of delay line 15-2. The contact $16_{2a}$ of switch 16-2 is connected through amplifier 18-2 to a maximum delay terminal of delay line 15-1 in the first circuit block 10-1.

Figure 6:
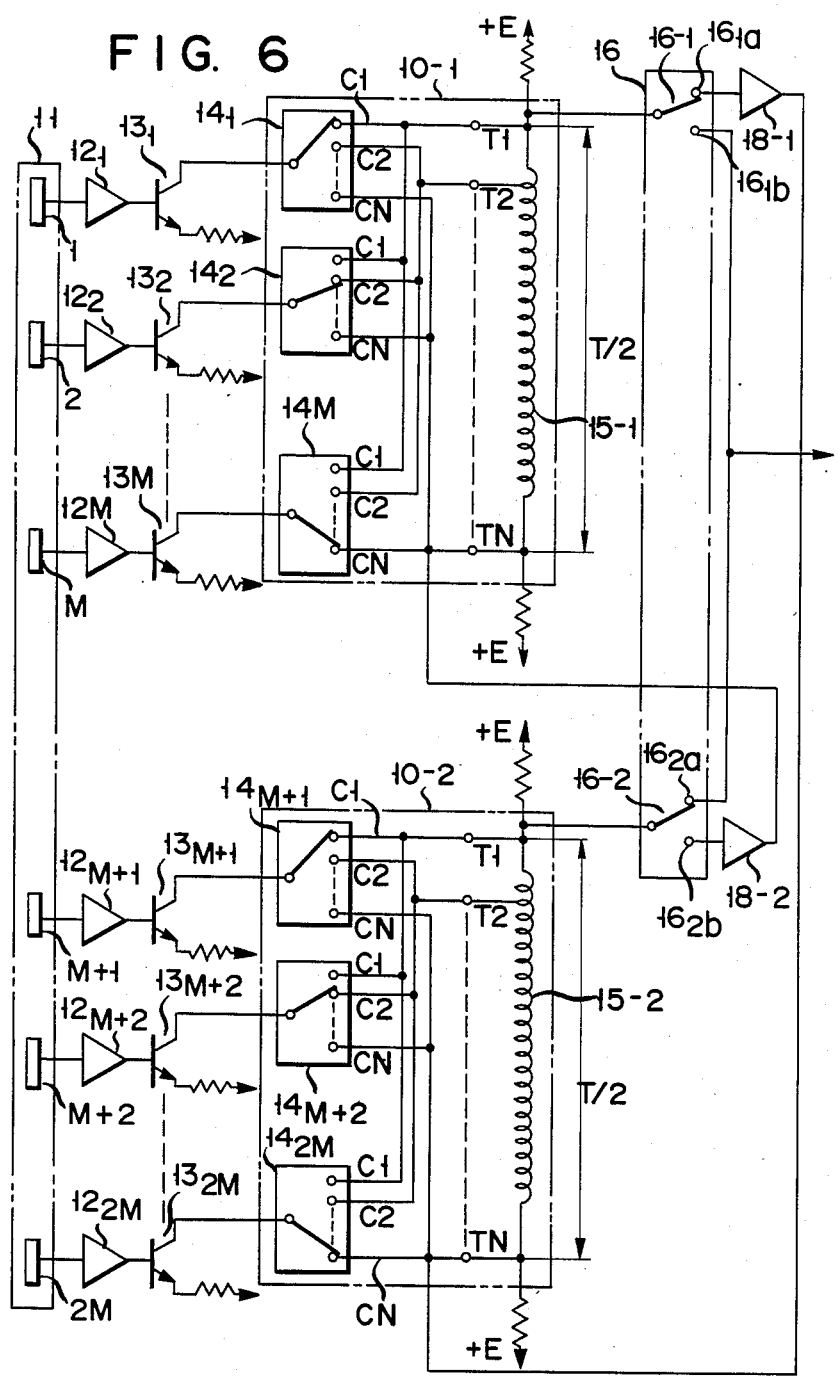
FIG. 6 is a circuit diagram of an ultrasonic scanning apparatus according to another embodiment of the present invention.

In the embodiment of FIG. 6, when switches 16-1 and 16-2 are connected to contacts $16_{1a}$ and $16_{2a}$, the echo signal passed through the delay line 15-1 in the block 10-1 is applied through contact $16_{1a}$ and amplifier 18-1 to the maximum delay terminal of delay line 15-2 in the block 10-2. The echo signal is delayed the maximum delay time T/2, by delay line 15-2. The delayed signal is output through contact $16_{2a}$ of switch 16-2 to the output terminal. On the other hand, the echo signal from the second circuit block 10-2 is applied through contact $16_{2a}$ to the output terminal. Thus, the echo signal from the first circuit block 10-1 is delayed by the delay line 15-1 in this block by an amount of delay of that delay line, and further delayed T/2 by delay line 15-2 of the second circuit block 10-2. The delay time as indicated by a shaded portion shown in FIG. 5 is secured by such a delay as the sum of the delays of delay lines 15-1 and 15-2.

When switches 16-1 and 16-2 are switched to contacts 16-1b and 16-2b, the echo signal from the block 10-1 is applied through contact 16-1b to the output terminal. The echo signal from the block 10-2 is applied to the maximum delay terminal of delay line 15-1 in the first circuit block 10-1, through contact 16-2b and amplifier 18-2. The echo signal is delayed the maximum delay time of T/2 by delay line 15-1, and is output through contact 16-1a to the output terminal. In this case, the echo signal from the first circuit block 10-1 is delayed by the delay line 15-1 in this block by the amount of delay of that delay line, and further delayed time T/2 by delay line 15-2 of the second circuit block 10-2. The delay time as indicated by a shaded portion shown in FIG. 5 is secured by such a delay as the sum of the delays of delay lines 15-1 and 15-2. In this case, the echo signal from the second circuit block 10-2 is delayed by the delay line 15-2 in this block by the amount of delay of that delay line, and further delayed time T/2 by delay line 15-1 of the first circuit block 10-1. The delay time as indicated by a shaded portion shown in FIG. 3 is secured by such a delay as the sum of the delays of delay lines 15-1 and 15-2.

As seen from the foregoing description, in the second embodiment, the delay lines of blocks 10-1 and 10-2 are used in place of the fixed delay line 17 used in the first embodiment. Such an arrangement can reduce the number of delay elements and cost to manufacture.

In these embodiments, the impedance of the fixed delay line 17 or the delay lines 15-1 and 15-2 of blocks 10-1 and 10-2 reduces approximately ½ a level of the signal applied to adder 19 or the output terminal. To compensate for this level drop, the amplifier 18 or the amplifiers 18-1 and 18-2, the gain of which is satisfactory for such level compensation, are provided at the output of the delay line 17 or contacts $16_{1a}$ and $16_{2b}$.

Figure 7:
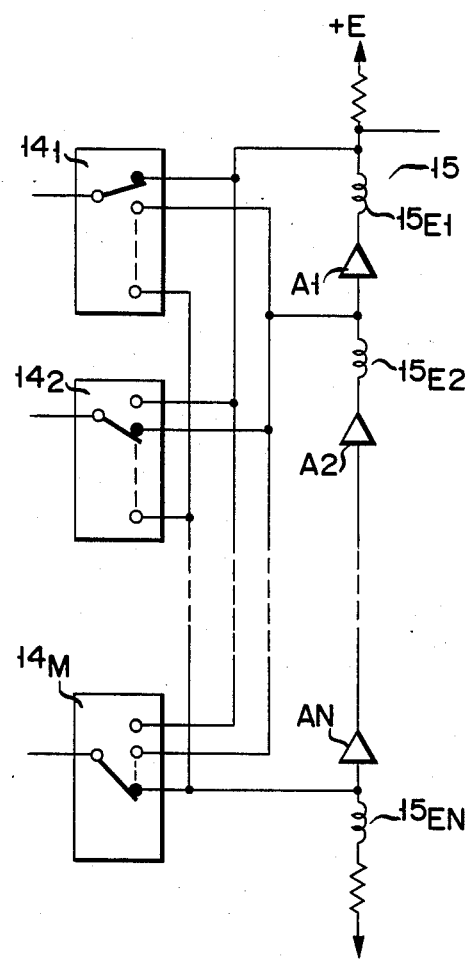
FIG. 7 is a circuit diagram of a switch circuit section used in an ultrasonic scanning apparatus according to a further embodiment.

Another embodiment of the present invention is illustrated in FIG. 7. As shown, the echo signal delaying section, which has delay lines 15-1 and 15-2, or these lines and another delay line 17 in the above-mentioned embodiments, includes delay line elements $15_{E1}$ to $15_{EN}$, and amplifiers A1 to AN each inserted between the elements. Provision of the amplifiers compensates for the level drop by the delay line elements. Of course, the compensating amplifiers may be provided for an appropriate number of delay line elements more than three.

As described above, the echo signals from a plurality of channels of the ultrasonic transducer probe are divided into at least two blocks. These blocked signals are subjected to the fixed delay line means. The number of switching elements for deflecting the ultrasonic beam can be reduced. This results in reduction of cost, and the stray capacitance and on resistance of the switching element.

What is claimed is:

1. An ultrasonic scanning apparatus for deflecting or steering ultrasonic beams in a plane, comprising:
    a transducer array having 2M ultrasonic transducer elements arranged in a row for converting ultrasonic echoes into electric echo signals, where M is integer;
    a first delay line means having a plurality of taps for providing different delay times;
    a first group of selectors connected to said first to Mth ultrasonic transducer elements of said transducer array, respectively, said selectors of said first group connecting the corresponding one of said first to Mth ultrasonic transducer elements to any one of said taps of said first delay line means for varying delay times of said echo signals of said first to Mth transducer elements;
    a second delay line means having a plurality of taps for providing different delay times;
    a second group of selectors connected to said (M−1)th to 2Mth ultrasonic transducer elements of said transducer array, respectively, said selectors of said second group connecting the corresponding one of said (M+1)th to 2Mth ultrasonic transducer elements to any one of said taps of said second delay line means for varying delay times of said echo signals of said (M+1)th to 2Mth transducer elements;
    a third delay line means having a predetermined delay time;
    means for adding output of said third delay line means and output of one of said first and second delay line means; and
    switching means for alternatively connecting the outputs of said first and second delay line means to said third delay line and said adding means.

2. An ultrasonic scanning apparatus according to claim 1, in which an amplifier is connected to the output of said third delay line means.

3. An ultrasonic scanning apparatus according to claim 1, in which said first and second delay line means each include a plurality of delay line elements with fixed delay times, and a plurality of amplifiers are each connected in series for at least one of said delay line elements.

4. An ultrasonic scanning apparatus according to claim 1, in which said first and second groups of selectors each include an analog switch.

5. An ultrasonic scanning apparatus for deflecting or steering ultrasonic beams in a plane, comprising:
    a transducer array having 2M ultrasonic transducer elements arranged in a row for converting ultrasonic echoes into electric echo signals, where M is integer;
    a first delay line means having a plurality of taps for providing different times;
    a first group of selectors connected to said first to Mth ultrasonic transducer elements to said transducer array, respectively, said selectors of said first group connecting the corresponding one of said first to Mth ultrasonic transducer elements to any one of said taps of said first delay line means for varying delay times of said echo signals of said first to Mth transducer elements;
    a second delay line means having a plurality of taps for providing different delay times;
    a second group of selectors connected to said (M+1)th to 2Mth ultrasonic transducer elements of said transducer array, respectively, said selectors of said second group each connecting the corresponding one of said (M+1)th to 2Mth ultrasonic transducer elements to any one of said taps of said second delay line means for varying delay times of said echo signals of said (M+1)th to 2Mth transducer elements; and
    switching means for alternatively inputting the output of said first delay line means to said second delay line means or vice versa.

6. An ultrasonic scanning apparatus according to claim 5, in which said switch means is connected to an amplifier for compensating the level drop of the echo signal.

7. An ultrasonic scanning apparatus according to claim 5, in which said first and second delay line means each include a plurality of delay line elements with fixed delay times, and a plurality of amplifiers are each connected in series for at least one of said delay line elements.

8. An ultrasonic scanning apparatus according to claim 5, in which said first and second groups of selectors each include an analog switch.

* * * * *